United States Patent [19]

Crowley

[11] Patent Number: 5,400,785
[45] Date of Patent: Mar. 28, 1995

[54] ACOUSTIC WINDOW AND SEPTUM FOR IMAGING CATHETERS

[75] Inventor: Robert J. Crowley, Wayland, Mass.

[73] Assignee: Boston Scientific Corp., Watertown, Mass.

[21] Appl. No.: 191,782

[22] Filed: Feb. 3, 1994

[51] Int. Cl.⁶ .................................................. A61B 8/12
[52] U.S. Cl. .................................. 128/662.06; 428/400
[58] Field of Search ...................... 128/660.01, 662.03, 128/662.06; 427/243, 245, 246; 428/400; 210/499, 500.21, 500.22

[56] References Cited

U.S. PATENT DOCUMENTS

| | | | |
|---|---|---|---|
| 4,349,033 | 9/1982 | Eden | 128/662.02 |
| 4,593,699 | 6/1986 | Poncy et al. | 128/662.03 |
| 4,815,470 | 3/1989 | Curtis et al. | 128/662.03 |

*Primary Examiner*—George Manuel

[57] ABSTRACT

A catheter, an acoustic septum and method for diagnosing body interiors utilizing the transmission and receiving of ultrasonic waves generated therewith. The catheter includes an elongated catheter sheath with a proximal end open to the atmosphere and an acoustic septum disposed at the distal end thereof. The septum is formed of a flexible sheet or tube of foraminous thermoplastic material, the depths of the foramina being at a predetermined ratio relative to their diameters. A hydrophilic coating is disposed on the sheet or tube and covers at least the edges of the foramina to allow the passage of liquid therethrough to fill the sheath. The coating is absorbent of the liquid to close the foramina and prevent the passage of liquids in either direction. A mechanism for generating and receiving ultrasonic waves is disposed within the distal end of the catheter and is in an operating relationship with the septum whereby to enable the mechanism to be bathed in the fluid and enable sonic transmissions.

21 Claims, 2 Drawing Sheets

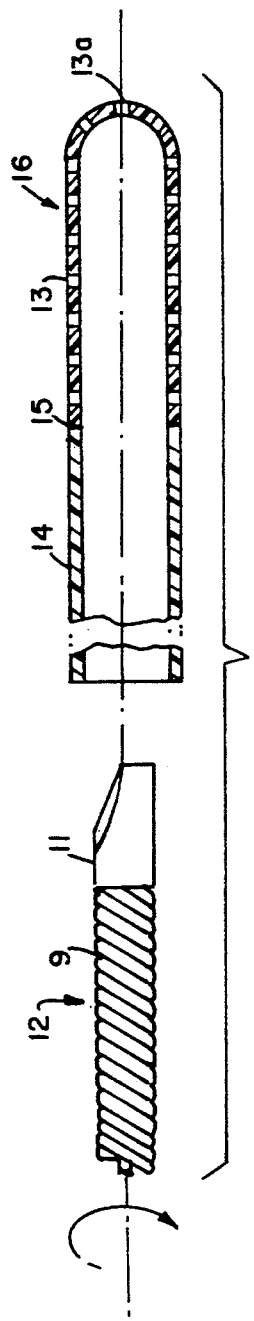
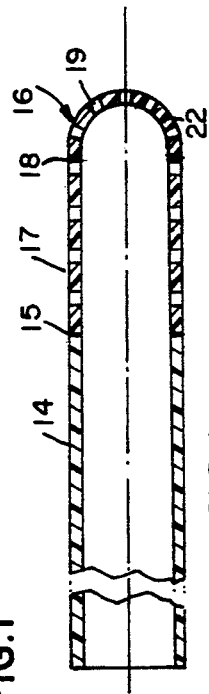
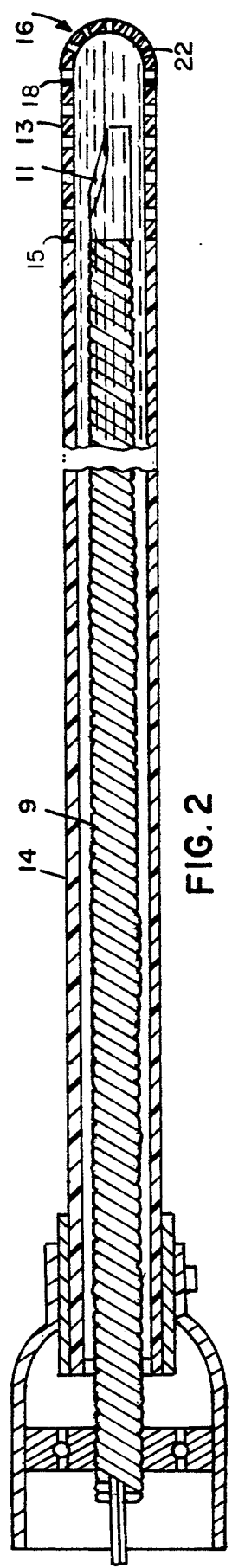

ACOUSTIC WINDOW AND SEPTUM FOR IMAGING CATHETERS

FIELD OF THE INVENTION

The present invention relates to an acoustic window that can act as a means to admit and retain fluids for use with ultrasonic imaging catheters and other catheters or guidewires that must be responsive to fluid contact. Ultrasonic imaging catheters are used for internally viewing body portions with ultrasonic waves generated by a generator/receiver disposed within the catheter. Such catheters involve the transmission and reception of ultrasonic waves through the catheter's walls and especially through a "window" after the catheter has been worked into various vessels of the body. Such ultrasonic catheters require a wave transmission fluid in the catheter between the transmitter, the receiver and the body part being examined.

DESCRIPTION OF THE PRIOR ART

Filling a catheter with a liquid to provide for low acoustic attenuation can be fairly difficult and time consuming. One way that has been used is to fill the catheter from its proximal end with the ultrasonic transmission fluid. Such methods, however, can entrap a bubble at the closed distal end of the catheter. Bubble formation is likely because of the narrow passageway of the catheter. A bubble in the wrong place may completely spoil any image generated by the imaging catheter.

As an alternative to filling the catheter from the proximal end, the patent to Crowley et al., U.S. Pat. No.5,002,059, discloses a disposable catheter which is formed from an acoustically transparent resilient flexible material in which the distal end of the catheter sheath is arranged to receive a septum thereon. The septum can be a cylindrically-shaped plug which can receive a needle-tipped syringe that is filled with an acoustically transmitting fluid. While such mechanisms for filling the catheter with transmission fluid have proven successful, I have found that the use of a hypodermic needle to inject the fluids can be eliminated through the use Of the acoustic septum and window of the present invention. I have also found that the use of the septum of the present invention is particularly useful to provide control of the acoustic waves emitted and received by the ultrasound catheter that would otherwise be difficult to provide due to its small size and limited aperture. The patent to Sieben et al., U.S. Pat. No. 5,243,988, also discloses an ultrasonic imaging device where the fluid is introduced into the proximal end of the catheter and excess fluid is poured out from the proximal end after the catheter is filled.

SUMMARY OF THE INVENTION

The present invention relates to an acoustic window and septum for transmitting and receiving ultrasonic waves and for controlling the passage of fluids. The window/septum comprises a coated flexible sheet or tube of foraminous plastic in which the depth of a foramen is at a predetermined ratio relative to its diameter. To provide for capillary action, the depths of the foramina are greater than the diameters. The diameter is between about $1\mu$ and $50\mu$ for each. The coating on the flexible sheet or tube is a soluble hydrophilic material such as gelatin, collagen or polyethylene oxide and has a thickness between about $0.1\mu$ and $10\mu$. It is deposited or impregnated on the sheet or tube by fluid conduction or polymerization where it can dry, harden or otherwise assume a solid state. The material absorbs liquid so that the coating, once hardened and dry, can absorb relatively large amounts of fluid when in contact with same, and further which, when saturated, causes a significant dimensional response creating a swelling of the then semi-solid or gelatinous material. The swollen material is effective to seal against the further flow of fluids while also providing for the transmission of sound waves with low attenuation. Materials that dry into a solid or semi-solid state are preferred because, prior to actual use of the device, organisms can grow in a fluid media of moist materials because such materials may contain nutrients. Although the coating covers the foramina, holes are left in each (or nearly each) foramen to allow for the passage of predetermined quantities of liquids through the flexible sheet or tube. When a predetermined quantity of liquid has passed through the sheet or tube, the coating swells to close the holes and prevent movement of fluids in either direction.

The composite material disclosed herein has a low acoustic attenuation and therefore is useful as an acoustic window for imaging catheters and guidewires that require fluid coupling for use. In addition to its being advantageous as an acoustic window, I have found that the lubricity of the surface of the catheter is enhanced because of the high liquid content of the window.

In the preferred embodiment of the present invention the ultrasonic imaging catheter comprises an elongated, disposable catheter tube having a closed distal end and an open proximal end. The acoustic septum/window is made so that the distal end (or a portion of the distal end) is formed from the coated, foraminous composite sheet material according to the present invention. The foraminous sheet or tube is acoustically transparent and resiliently flexible and will provide such transparency while maintaining a lubricous sterile barrier around an ultrasonic generator/receiver disposed within the catheter. The ultrasonic generator/receiver is in electrical communication with a signal generating and receiving device for displaying data that is generated.

To use the catheter of the present invention the attending physician can immerse the distal end of the catheter in water or saline for a sufficient time to enable the liquid to flow through the foramina of the acoustical window and fill the catheter through capillary action. The hydrophilic coating on the foraminous sheet or tube will swell and prevent fluids from either entering or emerging from the distal end of the catheter. In some cases if clearances are kept to a minimum, the emitting face of the transducer may be made to mechanically contact the inner surface of the foraminous wall which is effective to produce a low attenuation, low friction path and reduce the amount of fluids needed for operation of the transducer.

BRIEF DESCRIPTION OF THE DRAWINGS

FIG. 1 shows an exploded view, partially in cross-section, of a rotatable ultrasound generating and receiving device in axial alignment with a catheter sheath having an embodiment of an acoustical septum/window disposed at the distal end thereof and constructed in accordance with the principles of the present invention.

FIG. 1A shows another embodiment of the septum/window according to the present invention. This configuration can be substituted for the construction shown in FIG. 1.

FIG. 2 is a cross sectional side elevational view of the assembled elements shown in FIG. 1.

DESCRIPTION OF THE PREFERRED EMBODIMENTS

Figure 4:
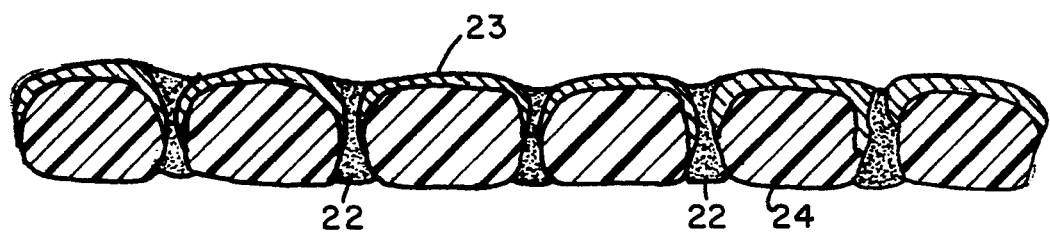
FIG. 4 is an enlarged cross-sectional view taken along the lines IV—IV of FIG. 3 and showing the foramina which allow the passage of fluids therethrough.

Referring now to FIG. 1 there is shown in an exploded view and ultrasound imaging catheter device 10 composed of a rotatable and slidably insertable ultrasound generating and receiving means 11 and a flexible catheter sheath 14 having a foraminous distal end 16 forming the acoustic septum/window 13. The acoustic septum/window 13 forms the entire distal end of the catheter including a leading end 13a and controls the passage of liquids therethrough as will be described hereinafter. It is attached to the sheath 14 at a joint 15 by a conventional adhesive seal or ultrasonic welding, as desired.

Referring to FIG. 1A of the drawing, an alternative embodiment of the present invention is shown. In this alternative embodiment an acoustic septum/window 17 is formed in a generally cylindrical shape with both ends being open. One open end of the acoustic septum/window 17 is joined to the catheter sheath 14 at a joint 15, as was the case with the embodiment of FIG. 1. In the FIG. 1A embodiment, a leading end 19 (formed of the same material as the sheath 14) is disposed at the distal end 16 of the catheter. The leading end 19 is adhesively attached to the other open end of the acoustic septum 17 or can be ultrasonically welded, as desired, at a joint 18. In this embodiment the septum 17 can be made in a cylindrical shape without the need for shaping it into a leading end as is the case with the embodiment of FIG. 1.

In FIG. 2 the assembled device is illustrated with the distal end 16 of the catheter being shown filled with a liquid, usually sterile water or a saline solution. The ultrasonic image generating receiving means comprises a single transducer element 11 directed at an angle to the axis of a drive shaft 9. A means (not shown) is provided for rotating the shaft at a speed in the order of 1800 rpm. To control emission in excess 10 megahertz, a position detecting means (not shown) is disposed at the proximal end of the drive shaft 9 for detecting the instantaneous angular position of the shaft 9 to represent the instantaneous angle position of the transducer. A T.V. monitor (not shown) which is responsive to return signals from the transducer 11 and to the position detecting means provides a display of an acoustical image based upon the signals detected by the transducer.

The catheter preferably uses a drive shaft 9 having an outer diameter through its length of about 1 mm. or less. The sheath 14 surrounds a segment of the distal end of the drive shaft and is adapted to apply dynamic viscous drag to the shaft during its rotation to enhance the mechanical fidelity of angular displacement between the proximal and distal ends of the catheter. The difference between the outer diameter of the shaft 9 and the inner diameter of the corresponding sheath portion is in the range of about 0.05 to 0.15 mm. The flexible foraminous member 13 which forms the acoustic septum encloses the transducer 11 and a portion of the drive shaft 9. The acoustic septum 13 is substantially transparent to acoustical energy transmitted and received by the transducer 11. The drive shaft 9 can have a liquid pumping screwform contour whereby the drive shaft 9 is exposed to liquid in the sheath and is driven in the direction tending to decrease the diameter of the outer coil, the outer surface of the coil being effective to pressurize liquid distally thereof. There is fluid communication between the liquid-filled space along the drive shaft 9 and the space occupied by the transducer 11 whereby the action of the screw form contour of the shaft is effective to prevent the liquid in which the transducer 11 is immersed from running to the proximal end of the catheter 20. The proximal end 20 is of conventional construction, well known to the art.

Figure 3:
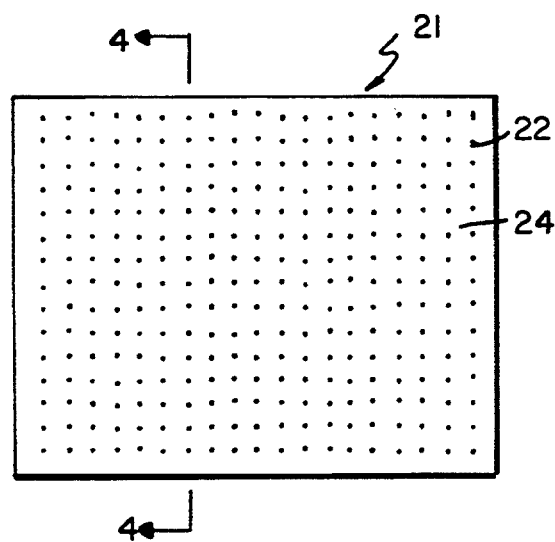
FIG. 3 is a plan view of the acoustic septum/window according to the present invention.

FIGS. 3 and 4 illustrate embodiments of the material used to form the acoustic septum 21 of the present invention. The septum 21 is formed as a sheet 24 of thermoplastic material such as an extrusion of polyethylene, polyamide or Nylon, the thickness of the extrusion being between about 0.01 and 0.5 mm. In this embodiment the thermoplastic sheet is rendered foraminous by drilling a matrix of micro-apertures 22 throughout the surface in a regular pattern. The holes 22 can also be made by ion beam etching. In the case of ion beam etching, the material is placed in a chamber next to an electrode and the eroding action of the ion beam removes small amounts of material. Also laser machining can be employed, most preferably excimer laser machining which makes hole diameters in the order of $1\mu$ or larger with high hole-to-hole repeatability. An advantage to such high precision hole-to-hole drilling is the ability to create matrices and grids. The grids may be rectilinear if desired. As an alternative to actual drilling of the material to make it foraminous, the material itself can be made of an to open cell porous, sponge-like or expanded polymer such as latex, silicone, polyurethane or other plastic material that absorbs water and therefore can be impregnated under pressure or by dipping into the expandable hydrophilic material while it is liquid.

Each of the apertures 22 within the foraminous sheet 24 have a diameter between about $1\mu$ and $50\mu$. A coating 23 (shown in FIG. 4) is disposed on the surface of the thermoplastic sheet 20. The coating 23 has a thickness between about 0.1 and $1\mu$ and is deposited so that the apertures 22 remain open during the procedure. The sheet 24 may be coated by dipping, spraying or painting the inner or outer surfaces. To prepare the surface, cleaning, etching or plasma treatments may be employed to aid surface adhesion. To prevent filling microapertures completely with the coating, air pressure may be applied to the sheet 24 soon after application. This has the desirable effect of creating rims around each aperture which aid the subsequent swelling and sealing of the microapertures because of their greater initial bulk.

Materials which have found to be suitable are those hydrophilic materials such as gelatin, collagen or polyethylene oxide. Fluids on one side of the sheet 24 enter into the apertures 22 and engage the coating 23 in the passage therethrough. When a predetermined quantity of fluids has passed through the apertures 22 they will swell and close thereby entrapping the water on the inside of the sheet and preventing its movement in one direction or the other. The illustrated in FIG. 3 can be rolled into a tube of any desired length and a tip can be sealed onto it as shown in FIG. 1A. Alternatively, the sheet can be draped upon a form of predetermined diameter and heated to cause it to form the shape shown in FIG. 1 thereby providing a tip 13a with a rounded end. The portion of the sheet which is extra is then cut away and the tip is sealed to the catheter for subsequent use.

It is apparent that modifications and changes can be made within the spirit and scope of the present invention. It is my intention, however, only to be limited by the scope of the appended claims.

As my invention I claim:

1. An acoustic septum for the conduction or transmission of acoustic waves and for controlling the passage of liquids, said acoustic septum comprising;
    a flexible tube or sheet of foraminous thermoplastic material having thickness, the depths of the foramina being substantially equal to said thickness at a predetermined ratio relative to their diameters, the depths being greater than the diameters;
    a hydrophilic coating disposed on said sheet or tube, said coating covering at least the edges of said foramina and allowing for the passage of liquid therethrough, said coating being absorbent of said liquid to close said foramina and prevent the passage of liquids through said foramina in either direction.

2. The acoustic septum according to claim 1 wherein said thickness is between about 0.01 and 0.5 mm. and the foramina have diameters between about 0.1 and 50$\mu$.

3. The acoustic septum according to claim 1 wherein the coating has a thickness between about 1 and 50$\mu$.

4. The acoustic septum according to claim 1 wherein the diameters of the foramina are between about 5 and 10 times the thickness of the hydrophilic coating.

5. The acoustic septum according to claim 1 wherein the thermoplastic material is a member selected from the group consisting of polyethylene and polyamides.

6. The acoustic septum according to claim 1 wherein the hydrophilic coating is a member selected from the group consisting of gelatin, polyethylene oxide and collagen.

7. The acoustic septum according to claim 1 wherein the foramina in said sheet or tube are arranged in a regular pattern.

8. The acoustic septum according to claim 1 wherein the foramina have diameters between about 0.1 and 10$\mu$.

9. The acoustic septum according to claim 1 wherein said sheet or tube has a cylindrical shape with both ends of the cylinder being open.

10. The acoustic septum according to claim 1 wherein said sheet or tube has a cylindrical shape with one end of said cylinder being open and the other end being formed as a tip.

11. A catheter for diagnosing body interiors utilizing the transmission and receiving of ultrasonic waves generated therewith, said catheter having a distal and a proximal end, said catheter comprising:
    an elongated catheter sheath having a proximal end open to the atmosphere and an acoustic septum disposed at a distal end thereof, said septum comprising a flexible sheet or tube of foraminous thermoplastic material having thickness, the depths of the foramina being substantially equal to said thickness and at a predetermined ratio relative to their diameters;
    a hydrophilic coating disposed on said sheet or tube, said coating covering at least the edges of said foramina and allowing the passage of liquid therethrough to fill said sheath, said coating being absorbent of said liquid to close said foramina and prevent the passage of liquids in either direction;
    means for generating and receiving ultrasonic waves disposed within the distal end of said catheter, said means being in an operating relationship with said septum whereby to enable said means to be bathed in said fluid and enable sonic transmissions.

12. The catheter according to claim 11 wherein said septum has a generally cylindrical cross section to form the distal end of said catheter.

13. The catheter according to claim 11 wherein said thickness is between about 0.01 and 0.5 mm. and the foramina have diameters between about 0.1 and 10$\mu$.

14. The catheter according to claim 11 wherein the coating has a thickness between about 1 and 50$\mu$.

15. The catheter according to claim 11 wherein the sheet or tube of thermoplastic material is a member selected from the group consisting of polyethylene and polyamides.

16. The catheter according to claim 11 wherein the hydrophilic coating is a member selected from the group consisting of gelatin, polyethylene oxide and collagen.

17. The catheter according to claim 10 wherein the foramina have diameters between about 0.01 and 10$\mu$.

18. A method for diagnosing body interiors utilizing the transmission and receiving of ultrasonic waves generated therewith, said catheter having a distal and a proximal end, said method comprising:
    disposing said catheter adjacent a body part to be examined, said catheter having a catheter sheath with a proximal end open to the atmosphere and an acoustic septum disposed at a distal end thereof, said septum comprising a flexible sheet or tube of foraminous thermoplastic material having thickness, the depths of the foramina being substantially equal to said said thickness and at a predetermined ratio relative to their diameters, said septum having a hydrophilic coating disposed thereon, said coating covering at least the edges of said foramina and allowing the passage of liquid therethrough to fill said sheath, said coating being absorbent of said liquid to close said foramina and prevent the passage of liquids in either direction;
    generating and receiving ultrasonic waves from a transmitter-receiver disposed within the distal end of said catheter through said septum whereby to enable said transmitter/receiver to be bathed in said fluid and enable sonic transmissions.

19. The method according to claim 18 wherein said flexible sheet or tube has said thickness between about 0.01 and 0.5 mm. and the foramina have diameters between about 0.1 and 10$\mu$, said coating having a thickness between about 1 and 50$\mu$.

20. The catheter according to claim 18 wherein the sheet or tube of thermoplastic material is a member selected from the group consisting of polyethylene and polyamides.

21. The catheter according to claim 18 wherein the hydrophilic coating is a member selected from the group consisting of gelatin, polyethylene oxide and collagen.

* * * * *